(12) United States Patent
Corrigan et al.

(10) Patent No.: US 11,366,046 B2
(45) Date of Patent: Jun. 21, 2022

(54) DETERMINE VISCOSITY OF FLUIDS USING A CAPILLARY CHANNEL

(71) Applicant: Hewlett-Packard Development Company, L.P., Spring, TX (US)

(72) Inventors: George H. Corrigan, Corvallis, OR (US); Adam Higgins, Corvallis, OR (US); Chantelle Domingue, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 445 days.

(21) Appl. No.: 16/476,187

(22) PCT Filed: Feb. 10, 2017

(86) PCT No.: PCT/US2017/017355
§ 371 (c)(1),
(2) Date: Jul. 5, 2019

(87) PCT Pub. No.: WO2018/147862
PCT Pub. Date: Aug. 16, 2018

(65) Prior Publication Data
US 2020/0041396 A1   Feb. 6, 2020

(51) Int. Cl.
*G01N 11/06* (2006.01)
*G01N 11/00* (2006.01)

(52) U.S. Cl.
CPC ........ *G01N 11/06* (2013.01); *G01N 2011/002* (2013.01)

(58) Field of Classification Search
None
See application file for complete search history.

(56) References Cited

U.S. PATENT DOCUMENTS

| 5,736,404 A * | 4/1998 | Yassinzadeh .......... G01N 11/04 422/130 |
| 6,818,184 B2 | 11/2004 | Fulwyler et al. |
| 7,188,515 B2 | 3/2007 | Burns et al. |
| 2006/0065044 A1 | 3/2006 | Tsang et al. |
| 2008/0121045 A1 | 5/2008 | Cole et al. |
| 2011/0297540 A1 | 12/2011 | Chu et al. |
| 2013/0086980 A1 | 4/2013 | Gadini et al. |

(Continued)

FOREIGN PATENT DOCUMENTS

| EP | 1186880 | 3/2002 |
| WO | WO-2008097578 | 8/2008 |

(Continued)

OTHER PUBLICATIONS

Srivastava, N et al., Electronic Drop Sensing in Microfluidic Devices: Automated Operation of a Nanoliter Viscometer, 2006.

*Primary Examiner* — Paul M. West
*Assistant Examiner* — Mark A Shabman
(74) *Attorney, Agent, or Firm* — HP Inc. Patent Department (57) ABSTRACT

The viscosity of a fluid may be determined using a flow rate determination. The flow rate may be determined based on fluid presence determinations within a capillary channel. Also, a temperature of an environment surrounding a capillary channel may be determined and signals may be transmitted to a thermal element responsive to the determined temperature.

20 Claims, 6 Drawing Sheets

(56) References Cited

U.S. PATENT DOCUMENTS

2014/0216140 A1    8/2014  Morhell et al.
2015/0377758 A1   12/2015  Lewis et al.

FOREIGN PATENT DOCUMENTS

| WO | WO-2011139719    | 11/2011 | |
|----|------------------|---------|---|
| WO | WO-2016100969 A1 * | 6/2016 | ............. G01N 11/08 |
| WO | WO-2016180964    | 11/2016 | |

* cited by examiner

DETERMINE VISCOSITY OF FLUIDS USING A CAPILLARY CHANNEL

INFORMATION

In certain types of situations, properties of fluids, such as viscosity, may be measured and/or estimated. Some methods and devices for measuring fluid properties may use relatively large fluid volumes. At times, fluid property measurement may be influenced by temperature such that, for example, temperature may cause estimation and/or measurement inaccuracy.

BRIEF DESCRIPTION OF THE DRAWINGS

Various examples are described below by referring to the following figures.

Reference is made in the following detailed description to accompanying drawings, which form a part hereof, wherein like numerals may designate like parts throughout that are corresponding and/or analogous. It will be appreciated that the figures have not necessarily been drawn to scale, such as for simplicity and/or clarity of illustration.

DETAILED DESCRIPTION

A times, it may be desirable to measure or estimate properties of a fluid (e.g., a liquid or a gas). For example, it may be useful to have a measurement or an estimate of a fluid's viscosity. Some methods of determining fluid properties, such as a viscosity of a fluid, may comprise use of a gravimetric capillary tube device, a rotational disk, a Stabinger (concentric-tube) device, a rolling/falling ball device, etc. Methods and devices, such as the foregoing, that use large quantities of fluids may be less useful in some cases, such as in a lab-on-a-chip use case.

To illustrate, an example case involving measuring viscosity of blood is presented. In this example case, it may be desirable to, for instance, measure blood viscosity using as little fluid as possible. For instance, measuring the viscosity and/or coagulation of blood using a blood sample in the nano- and microliter range might be one example use case. As may be appreciated, measuring blood viscosity of a nanoliter or microliter of blood using a gravimetric capillary tube device, a rotational disk, a Stabinger device, and/or a rolling/falling ball device may be impracticable. Thus, there may be a desire for methods and/or devices capable of measuring fluid properties of small sample volumes (e.g., a nanoliter, a microliter, etc.) of a fluid.

However, devices capable of measuring and/or estimating properties of a fluid using small sample volumes may, in some cases, be susceptible to temperature variations or fluctuations, for example, that may affect property measurements and/or estimates. In fact, some fluid properties may vary in response to changes in temperature. For example, viscosity of a fluid may vary with temperature. In one case, then, a fluid may be less viscous at a first temperature than at a second temperature. There may therefore be a desire for a method and/or a device capable of monitoring and/or controlling temperature while measuring and/or estimating fluid properties.

In addition to temperature susceptibility, fluid property measurement and estimation devices may also encounter potential space constraints that may present designers with certain challenges. For example, in the context of a lab-on-a-chip, it may be desirable to limit and/or reduce device components that may be potentially superfluous, such as to free up space on a chip for additional lab measurement components, for example. As referred to herein, a "chip" or "microchip" refers to a plurality of components forming circuits arranged on a substrate, often a portion of a silicon wafer. By way of non-limiting illustration, and as shall be discussed hereinafter, it may be possible to measure or estimate properties of a fluid without use of fluid pumps or injection mechanisms. Not using fluid pumps or injection mechanisms may free up space on a chip for other components, for example. Thus, there may be a desire for devices and/or methods that may operate without, for example, fluid pumps or injection mechanism.

In light of the foregoing, a device, system and/or method is proposed that may be capable of measuring or estimating properties of fluids using small volumes of fluids (e.g., on the range of nano- or microliters, for example). In one implementation, an example device may comprise a capillary channel through which a fluid may travel. Measurements may be made as the fluid traverses the capillary channel, and the measurements may be used in order to determine certain properties of the fluid. For example, measurements of a sample fluid may be made to determine a flow rate, which may be used, at least in part, to estimate a viscosity of the fluid.

Flow rate may be estimated based a plurality of fluid position measurements. For example, an array of sensors (e.g., electrochemical sensors, capacitive sensors, or optical sensors) may be arranged along a capillary channel and may provide signals indicative of fluid position. Taking the case of an array of electrochemical sensors to illustrate, a pair of electrodes may be deposited along a capillary channel. At times at which no fluid is present in a capillary channel, the electrodes may act as an open circuit such that no current travels between electrodes of the electrode pair of a sensor. In contrast, at times at which a fluid is present in a capillary channel, the electrodes may act as a closed circuit, and electrons may travel through the fluid between the pair of electrodes. Fluid position measurements may be used in conjunction with timing values in order to determine flow rate. And as shall be discussed in greater detail hereinafter, flow rate may be used to determine a viscosity value of a fluid.

At times, reliable measurements of flow rate of a fluid may depend, at least in part, on a force causing the fluid to travel through the capillary channel. In one example, fluid may be caused to traverse a capillary channel at a constant flow rate and/or using a constant force, such as by injecting the fluid using a pump or injection mechanism. However, in cases that do not use a fluid pump, capillary forces may be used to cause movement of fluids through a capillary channel. As a fluid advances along a capillary channel, it may be that due to an increased volume of fluid in the capillary channel, greater frictional forces, etc., a greater amount of force may need to be exerted upon the fluid in order to maintain flow rate. Consequently, for property measurement devices that use capillary forces (e.g., rather than a pump), flow rate of a fluid may decrease the further that the fluid advances along the capillary channel.

It may be that in some cases of the present disclosure, complementary metal-oxide semiconductor (CMOS) devices may be used to measure properties of a fluid, such as using a lab-on-a-chip. Example CMOS lab-on-a-chip devices may be capable of using capillary forces to provide a force to a fluid travelling through a capillary channel, and may have a plurality of sensors (e.g., a sensor array) arranged along the capillary channel to measure, for example, flow rate and viscosity of the fluid. Additionally, it is noted that CMOS fabrication methods may be used to form such devices.

Figure 1:
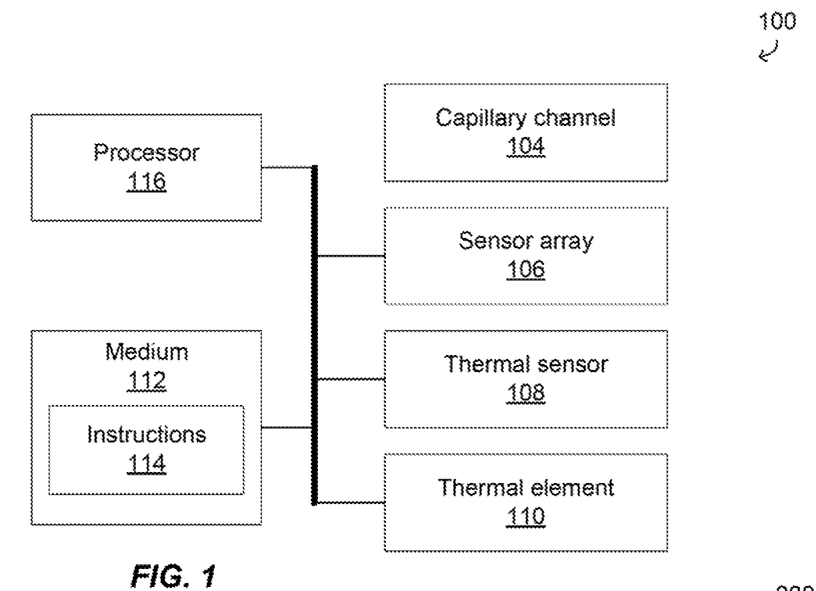
FIG. 1 is an example block diagram of an example system for determining fluid properties.

Turning now to FIG. 1, a computing system 100 is illustrated comprising a capillary channel 104, a sensor array 106, a thermal sensor 108, a thermal element 110, a processor, 116, a computer-readable medium 112 having instructions 114 stored thereon. Sensor array 106 may comprise a plurality of sensors (e.g., electrochemical sensors) arranged along capillary channel 104 and capable of detecting a presence of a fluid within capillary channel 104. Sensor array 106 may be communicably coupled to processor 116, such as to enable transmission and/or reception of signals. For example, one or more sensors of sensor array 106 may transmit one or more signals to processor 116 indicative of a presence of a fluid at the one or more sensors of sensor array 106. In an implementation using electrochemical sensors, an electrode pair may be arranged to be in proximity to fluid passing through capillary channel 104, so that a fluid in capillary channel 104, if present, enables electron travel from one electrode to another of the electrode pair. At processor 116, one or more signals may be received responsive to electrons traversing an electrode pair. The received signals may be used in order to determine, for example, a presence of a fluid in a capillary channel, an estimate of flow rate, an estimate of viscosity of a fluid, etc.

As shall be discussed hereinafter, capillary channel 104 may serpentine across a surface of a chip, such as to provide a greater distance for a fluid to travel through capillary channel 104. For instance, a greater distance may provide greater opportunity to measure fluid presence or flow rate, for example. Other arrangements of capillary channel 104, in addition to a straight and a serpentine arrangement, may include a spiral arrangement, for example.

Thermal sensor 108 may comprise an element capable of measuring a temperature of an environment surrounding capillary channel 104 (or providing measurements to a processor usable by the processor to estimate a temperature). By way of example, sample thermal sensors 108 may comprise a silicon bandgap temperature sensor, precision monolithic temperature sensors (e.g., including, but not limited to, a metal trace covered with a dielectric), temperature sensitive thin film metals, polysilicon resistors, diffusion resistors, etc. Thermal sensors 108 may be arranged in proximity to capillary channel 104 or physically contacting capillary channel 104, for example. One or more signals may be transmitted from thermal sensor 108 to processor 116, the one or more signals being indicative of a temperature of an environment surrounding thermal sensor 108 and/or capillary channel 104, or may be usable to estimate a temperature of the environment surrounding thermal sensor 108 and/or capillary channel 104.

Thermal element 110 may comprise a component capable of imparting heat to a device and/or generally controlling a temperature of an environment surrounding capillary channel 104. In one case, one or more signals may be transmitted from processor 116 to thermal element 110 and due, at least in part, to the materials of thermal element 110 (e.g., material resistivity), thermal element 110 may impart heat to a region surrounding capillary channel 104. In one example, rather than being distinct components, thermal element 110 and thermal sensors 108 may comprise an integrated component. That is, a thermal element may be capable of both sensing temperature and heating a region. Furthermore, in one example, it may be possible to cool a system, such as system 100, using fluid cooling methods, passive cooling, and/or thermal transfer features.

Computer-readable medium 112, which comprises a non-transitory medium, may comprise a memory capable of storing instructions, such as instructions 114, and signals received from processor 116, sensor array 106, and thermal sensor 108. Instructions 114 may comprise instructions to estimate a flow rate, a change in flow rate, a fluid viscosity, a change in fluid viscosity, a coagulation of a fluid, a temperature of an environment surrounding capillary channel 104, etc., based, at least in part, on signals received from sensor array 106, thermal sensor 108, and/or processor 116.

Figure 2:
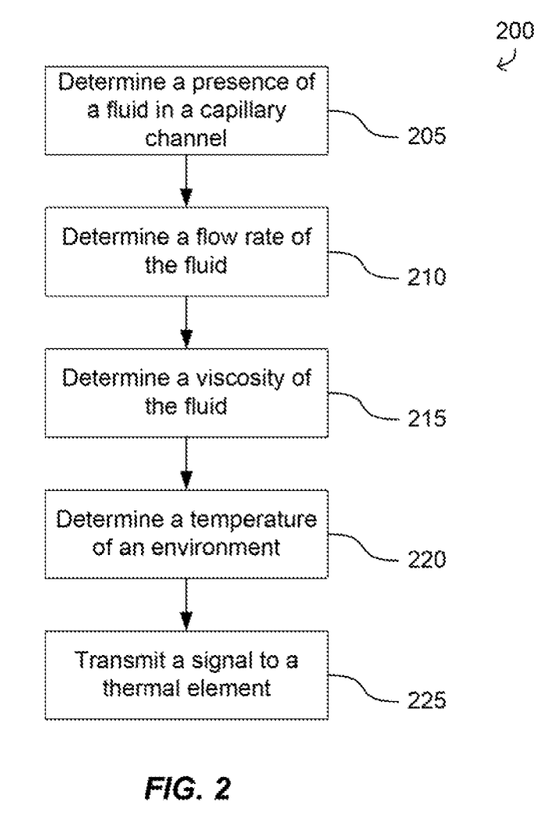
FIG. 2 is an example flow chart of a method for determining fluid viscosity.

In one implementation, processor 116 may fetch instructions from computer-readable medium 112 that, when executed, may use signals received from sensor array 106 in order to determine a flow rate for a fluid. FIG. 2, for example, illustrates a method 200 comprising, at block 205, determining a presence of a fluid in capillary channel 104. In one example, this may comprise instructions to use signals received from sensor array 106 to determine a location along capillary channel 104 at which a fluid may be detected. At times, the position determination may be associated with a time value (e.g., clock signal value).

TABLE 1

| Sensors | $s_1$ | $s_2$ | $s_3$ | $s_4$ |
| --- | --- | --- | --- | --- |
| $t_0$ | 0 | 0 | 0 | 0 |
| $t_1$ | 1 | 0 | 0 | 0 |
| $t_2$ | 1 | 1 | 0 | 0 |
| $t_3$ | 1 | 1 | 1 | 0 |
| $t_4$ | 1 | 1 | 1 | 1 |

Table 1 illustrates sample position determinations corresponding to sensor positions of sensor array 106 comprising four sensors (e.g., electrode pairs) $s_1$-$s_4$ at five sample times, $t_0$-$t_4$. For purposes of the present discussion, it is assumed that sensor $s_1$ is located closest to the start of capillary channel 104 and that sensor $s_4$ is located furthest from the start of capillary channel 104. A '1' value in Table 1 indicates fluid detection at a corresponding sensor and a '0' value indicates that no fluid is detected at the corresponding sensor.

In the illustrative example of Table 1, at a time $t_0$, fluid is detected at none of sensors $s_1$-$s_4$ of sensor array 106. Thus, for example, processor 116 may execute instructions from instructions 114 and, using signals from sensor array 106 illustrated in the first row of Table 1, determine that no fluid is in capillary channel 104. At a time $t_1$, fluid may be detected at sensor $s_1$, but not at sensors $s_2$-$s_4$. Thus, for example, processor 116 may execute instructions from instructions 114 and, using signals from sensor array 106 (illustrated in the second row of Table 1), determine that there is fluid in capillary channel 104 and further that the detected fluid is positioned at a location corresponding to sensor $s_1$.

At a time $t_2$, fluid may be detected at sensors $s_1$ and $s_2$, but not at sensors $s_3$ or $s_4$. Thus, for example, processor 116 may execute instructions from instructions 114 and, using signals from sensor array 106 (illustrated in the third row of Table 1), determine that there is fluid in capillary channel 104 and further that the detected fluid extends from at least sensor $s_1$ to sensor $s_2$. Processor 116 may thus determine that the fluid is located at a position in capillary channel 104 extending from sensor $s_1$ to sensor $s_2$.

At a time $t_3$, fluid may be detected at sensors $s_1$-$s_3$, but not at sensor $s_4$. Thus, for example, processor 116 may execute instructions from instructions 114 and, using signals received from sensor array 106 (illustrated in the fourth row of Table 1), determine that there is fluid in capillary channel 104 and further that the detected fluid is detected so as to extend from at least sensor $s_1$ to sensor $s_3$. Processor 116 may thus determine that the fluid is located at a position in capillary channel 104 extending from sensor $s_1$ to sensor $s_3$.

At a time $t_4$, fluid may be detected at sensors $s_1$-$s_4$. Thus, for example, processor 116 may execute instructions from instructions 114 and, using signals received from sensor array 106 (illustrated in the fifth row of Table 1), determine that there is fluid in capillary channel 104 and further that the detected fluid is positioned so as to extend from at least sensor $s_1$ to sensor $s_4$.

In one example, the determinations from block 205 of method 200 may be stored, such as in computer-readable medium 112. As noted above, the determinations may be associated with one or more timing values, such as those illustrated in Table 1 by way of non-limiting example.

Returning to instructions 114 of FIG. 1, instructions may be fetched and executed by processor 116, such as to determine a flow rate of a fluid, such as illustrated by block 210 in FIG. 2. By way of non-limiting example, values stored, such as in the form of a signal or a state, responsive to the determination at block 205, may be used to determine a flow rate of a fluid. To illustrate, a flow rate of a fluid may be estimated by determining a difference in time $\Delta t$ (e.g., $t_1-t_0$) as compared to a difference in position. Thus, for example, and using the sample values from Table 1, a rate may be determined at a time $t_1$ to correspond to $(p_1-p_0)/(t_1-t_0)$, where p refers to a position corresponding to a sensor number. Thus, for example, $p_1$ corresponds to a position of $s_1$, etc. This relation may be expressed more generally as:

$$\text{flow rate} = \frac{(p_x - p_{x-1})}{(t_i - t_j)}$$

where x refers to a sensor number, i refers to a unit of time, and j refers to a unit of time corresponding to position $p_{x-1}$. For example, in some cases it may take multiple units of time for a fluid to travel between position $p_{x-1}$ and $p_x$, which may be neighboring or adjacent sensor positions along a capillary channel.

In one implementation, instructions 114 may include instructions to store the result of block 210 of method 200 in computer-readable medium 112. The determined flow rates may be associated with timing values. Thus, for example, at a first time, a fluid may be determined to have a first flow rate, and at a second time the fluid may be determined to have a second flow rate different from the first flow rate. In one example, a flow rate of a fluid may decrease as the fluid advances through capillary channel 104.

Returning to FIG. 1, instructions 114 may include instructions that may be fetched and executed by processor 116 to determine a viscosity of a fluid, such as illustrated by block 215 of method 200 in FIG. 2. In one implementation, determinations made at blocks 205 and 210 may contribute to a determination at block 215. For example, a relationship may exist between flow rate and viscosity and thus flow rate determinations made, for example, at processor 116, may be used, at least in part, to estimate fluid viscosity.

If it is assumed that capillary channel 104 is arranged horizontally and has a cylindrical form, fluid flow due to capillary forces through capillary channel 104 may be described using the following relation (Washburn relation):

$$L^2 = \frac{\gamma \cos(\varphi) D}{4\mu} t \quad (1)$$

where L is a distance traveled through capillary channel 104, $\gamma$ is the surface tension (and may be a known value for different fluids), $\varphi$ is the contact angle of the liquid on the capillary material (e.g., the angle at which a liquid meets a solid surface, such as the wall of a capillary channel), D is the capillary diameter, t is the time and $\mu$ is the viscosity. As described above, sensor array 106 may provide measurements usable by processor 116 to determine L and the corresponding time t. It is noted that a similar relation may be obtained for a rectangular capillary channel, etc.

Figure 3:
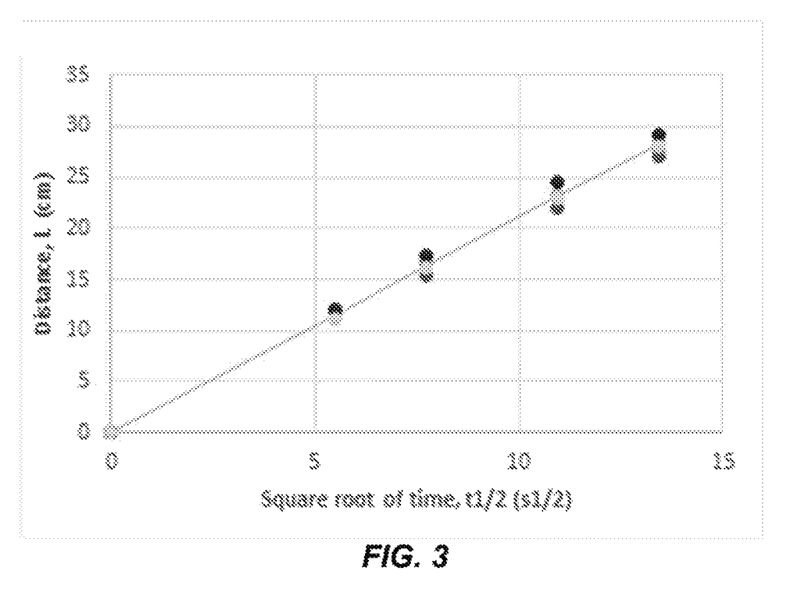
FIG. 3 is an example plot illustrating a relationship between fluid position in a capillary channel and time.

FIG. 3 is a plot illustrative of movement of water through a capillary channel of diameter D according to relation (1). According relation (1), the slope of the line may be described as:

$$\text{slope} = \frac{\sqrt{D}}{2} \sqrt{\gamma \cos(\varphi)} \sqrt{1/\mu} \quad (2)$$

The term $$\frac{\sqrt{D}}{2}$$

refers to geometrical properties of the capillary (e.g., diameter D for a cylindrical capillary channel). The term $\sqrt{\gamma\cos(\varphi)}$ is related to an interaction between the fluid and the walls of capillary channel 104 (e.g., surface tension and contact angle), and the term $\sqrt{1/\mu}$ contains a measure of viscosity. Geometrical parameters of a capillary channel, such as capillary channel 104, may be defined by the microfabrication process and may be confirmed by testing capillary channel 104 with a fluid having a known viscosity, surface tension, and contact angle, for example. In the case of a vertically-oriented capillary channel, the second term (e.g., relating to surface tension and contact angle) of relation (2) for a fluid-of-interest may be determined using an equilibrium wicking test, for example. For this, force balance at equilibrium may be expressed as:

$$\gamma \cos(\varphi) = \frac{Dh\rho g}{4} \quad (3)$$

where h is the vertical distance traveled by the fluid into the capillary, $\rho$ is the fluid density, and g is the acceleration of gravity. It is noted that in some cases, a same sensor array arrangement may be used with a vertically oriented capillary to determine h, which can then be used to determine $\gamma \cos(\varphi)$.

Returning to the slope relation, relation (2), viscosity of the fluid may be determined based, at least in part, on determinations of the first and second terms (e.g., $$\frac{\sqrt{D}}{2} \text{ and } \sqrt{\gamma \cos(\varphi)}\bigg).$$

For example, determining the viscosity of a fluid may be done based, at least in part, on a plot of distance L versus the square root of time, such as illustrated in FIG. 3. For example, in one case, the $$\frac{\sqrt{D}}{2}$$

term may be known, such as based on a process of fabrication. Further, fluid properties, such as surface tension and contact angle may be known for a fluid to be tested. Using these values, it may be possible to solve for $\mu$.

Returning to FIG. 1, instructions 114 may comprise instructions to determine a temperature of an environment, such as shown at block 220 of method 200 in FIG. 2. While FIG. 2 shows blocks 220 and 225 occurring in series with the determinations at blocks 205, 210, and 215, it is noted that blocks 220 and 225 may occur in parallel. Indeed, in one example, a device may monitor and regulate the temperature of an environment surrounding capillary channel 104 while determinations as to, for example, fluid presence, flow rate, and/or viscosity are made for a fluid.

Determining a temperature of an environment, such as illustrated at block 220, may comprise reception of one or more signals from temperature sensors, such as thermal sensor 108 illustrated in FIG. 1. In one case, signals received from thermal sensor 108 may be used to estimate a temperature of an environment surrounding capillary channel 104. A temperature determination may be stored in a computer-readable medium, such as computer-readable medium 112 of FIG. 1. In one example, temperature determinations may be associated with time values, such as to enable determinations as to changes in temperature per unit time, by way of example.

Returning to FIG. 1, instructions 114 may comprise instructions to transmit signals to a thermal element, such as shown at block 225 of method 200 in FIG. 2. The signals transmitted to a thermal element, such as thermal element 110, may be based, at least in part, on signals received from thermal sensor 108, and the signals may be transmitted to control temperature of an environment surrounding a capillary channel, such as capillary channel 104. In one implementation, a temperature determination may be used in order to identify a need to change a temperature of the environment surrounding capillary channel 104. For example, to change a temperature, one or more signals may be transmitted to thermal element 110. In one case, electrons flowing through thermal element 110 may generate heat that may be given off in a region surrounding thermal element 110. It may be that in some cases, different signal values (e.g., different current or voltage values) may engender different levels of heat generation. Thus, for example, responsive to temperature determinations outside of an acceptable threshold, signals of greater magnitude may be transmitted to thermal element 110. Transmission of such signals to thermal element 110 may be based on a desire to maintain temperature within an acceptable threshold, such as to avoid variations in viscosity estimations for a fluid.

Figure 4:
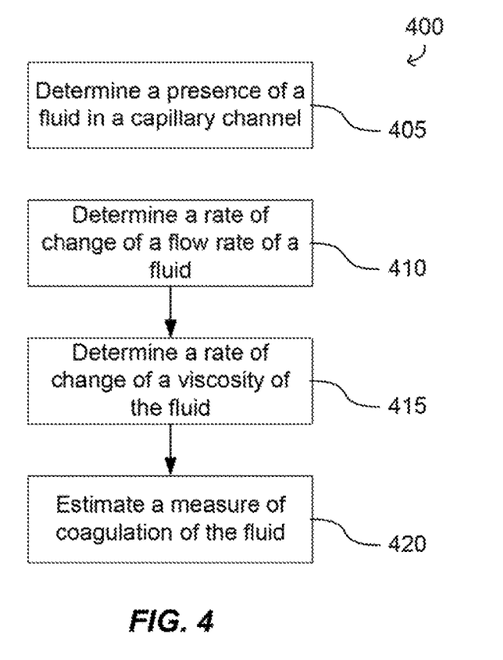
FIG. 4 is an example flow chart of a method for estimating a measure of coagulation of a fluid.

At times, it may be desirable to determine other parameters of a fluid. By way of example, in the context of lab-on-a-chip devices, there may be a desire to measure or estimate coagulation of a sample of blood of a patient. FIG. 4 illustrates a sample method 400 for estimating a coagulation of a sample of blood of a patient. Sample method 400 may be accomplished using system 100 illustrated in FIG. 1, by way of example.

In one implementation, at block 405 of sample method 400, a presence of a fluid in a capillary channel, such as capillary channel 104, may be determined, similar to the above discussion of sample method 200. By way of non-limiting example, one or more sensors of an array of sensors, such as sensor array 106, may be usable to detect a presence and/or position of a fluid in a capillary channel, such as capillary channel 104. The sensor readings may be associated with one or more time values and/or may be stored in a computer-readable medium.

The sensor readings may be used to determine a rate of change of a flow rate of a fluid, such as at block 410 of method 400. As was noted above, fluids impelled through a capillary channel by capillary forces may experience a decrease in flow rate proportional to a distance traveled through the capillary channel. Thus, for a given fluid, there may be an expected rate of change of a flow rate. For example, water may experience an expected rate of change of a flow rate as it travels through a capillary channel, impelled by capillary forces. Likewise, citrated blood (e.g., blood plasma mixed with sodium citrate to avoid clotting) may also have an expected rate of change of flow rate as it is impelled through a capillary channel by capillary forces. Consequently, for a given fluid, deviations from an expected rate of change of flow rate may indicate a change in viscosity. And, assuming that the temperature surrounding the capillary channel remains approximately constant, it may be determined that the change in viscosity is due to coagulation of the fluid. In the case of blood samples, it may be desirable to determine a rate of coagulation to compare with an expected rate (such as to identify whether a patient has a clotting disorder, by way of example).

Thus, at block 415 a determination may be made as to a rate of change of viscosity of a fluid sample. By way of example, as viscosity estimates are made and/or stored, such as discussed in method 200, changes in viscosity may be detected. For instance, as a fluid sample traverses a capillary channel, it may be expected that the fluid will have an approximately same viscosity estimate at different times. However, if it is determined that a viscosity of the fluid sample changes during its traversal of a fluid channel, then those changes of viscosity may be used to estimate a measure of coagulation of the fluid sample.

Figure 5:
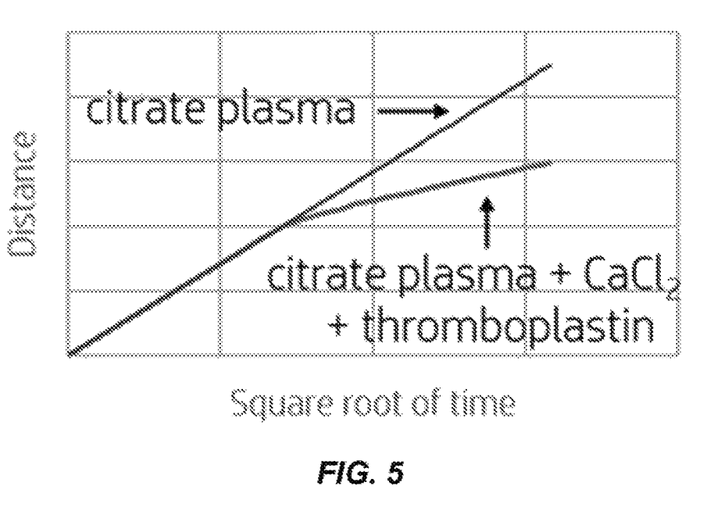
FIG. 5 is an example plot illustrating a prothrombin time.

In one example, and as illustrated by block 420 of sample method 400, an estimate of a measure of coagulation may be made, such as using viscosity rate of change determinations. With regards to determining a coagulation of blood, two example tests that may be used to assess blood coagulation properties may comprise: a prothrombin time assay and an activated partial thromboplastin time (aPTT) assay. Both of these tests comprise measuring a time for a blood sample to coagulate. FIG. 5 illustrates hypothetical results for a blood sample being tested to determine a measure of coagulation.

In the case of estimating coagulation of a blood sample, citrated plasma is not expected to clot. Consequently, a linear relationship between the distance traveled into the capillary and the square root of time would be expected for a citrated plasma sample. As such, viscosity would also be expected to remain constant. However, when $CaCl_2$) and thromboplastin are added to citrated plasma, coagulation is expected to occur. Consequently, a time lag between the addition of thromboplastin to the plasma and coagulation may be determined using a blood sample. The time lag may be referred to as the prothrombin time. FIG. 5 illustrates a time lag (lower arc) as a decrease in the slope and indicates that fluid moves more slowly through the capillary as coagulation occurs based on increases in viscosity. The time at which this decrease in slope occurs is expected to correlate with the prothrombin time. Deviations from this expected time may indicate deviations in a measure of coagulation that may potentially indicate clotting disorders. For example, if a blood sample travels a greater distance before changes in viscosity begin to occur, then a Δt in prothrombin time may indicate that the blood sample is clotting too slowly (or not at all). In contrast, determinations that a blood sample travels a lesser distance through a capillary channel before experiencing changes in viscosity may indicate that the blood sample is clotting too quickly. The calculation of delay before changes in viscosity occur may thus offer a potentially useful indication of blood health. These determinations may be made by comparing a determined prothrombin time with an expected prothrombin time, for example.

Figure 6:
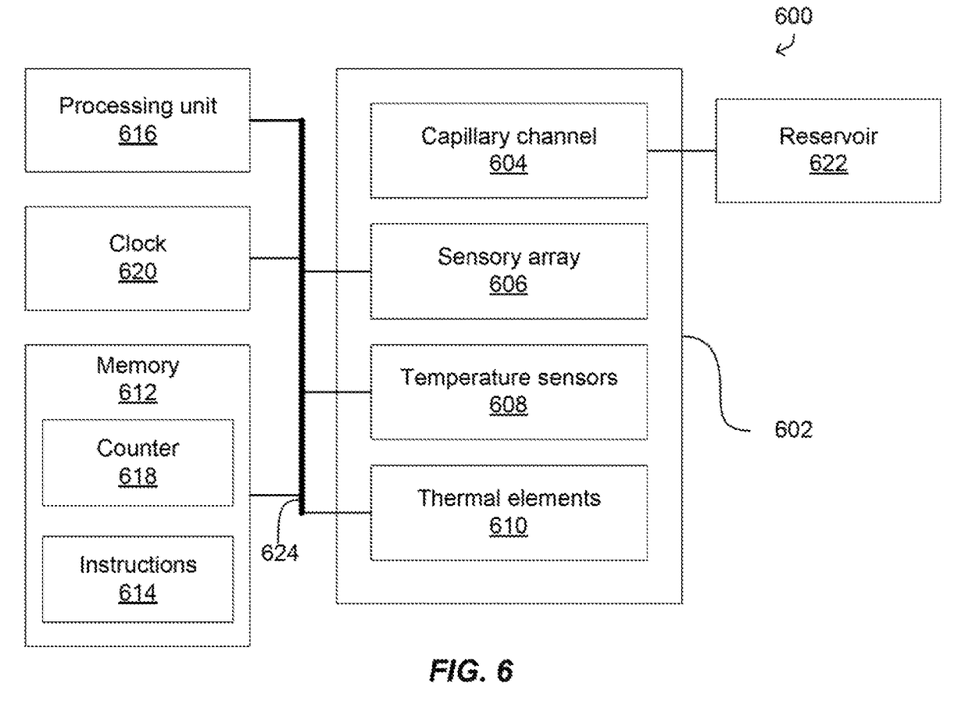
FIG. 6 is an example block diagram of a system for determining fluid properties.

FIG. 6 illustrates a system 600 for determining parameters of a fluid sample, such as viscosity or coagulation. System 600 may comprise a device 602, which may comprise a CMOS device, and might be a lab-on-a-chip device, for example. Device 602 may comprise a capillary channel 604. In one example, capillary channel 604 may be formed as an integrated component of device 602 (e.g., such as by deposition of successive layers of polymer over a substrate). Capillary channel 604 may be in fluid communication with reservoir 622, which may comprise a component capable of retaining a fluid. In one case, for example, a valve or like mechanism may be used to retain a fluid within reservoir 622 or to allow access to capillary channel 604.

Sensor array 606 may comprise an array of uniformly spaced sensors, such as electrochemical, capacitive, or optical sensors, capable of detecting a presence of a fluid along capillary channel 604, similar to the discussion of FIGS. 1 and 2, above. For example, signals may be transmitted to processing unit 616 indicative of a presence of a fluid in capillary channel 604. Instructions, such as from instructions 614, may be executed by processing unit 616 to determine a presence of a fluid, determine a flow rate, determine a rate of change of a flow rate, determine a viscosity, determine a rate of change of viscosity, and/or determine a measure of coagulation (e.g., prothrombin time). Furthermore, temperature sensors 608 may comprise a plurality of temperature sensors capable of determining a temperature of an environment surrounding capillary channel 604, and transmitting signals indicative of temperature to processing unit 616. Responsive to which, instructions may be executed by processing unit 616 to determine a temperature corresponding to the signals received from temperature sensors 608. One or more signals may be transmitted to thermal elements 610, such as to change a temperature of an environment surrounding capillary channel 604. Signals transmitted and/or received in system 600 may traverse a conductive medium, such as bus 624.

System 600 also comprises a clock 620 and a counter 618. In one example, clock 620 and counter 618 may be used in conjunction with other components of system 600 to determine fluid presence, flow rate, rate of change of flow rate, viscosity, rate of change of viscosity, coagulation, etc. By way of example, clock 620 and counter 618 may be used to associate a time value with a presence determination. In one example, processing unit 616 may fetch instructions from instructions 614 that, when executed, enable processing unit 616 to determine of a flow rate of a fluid, such as discussed above in relation to block 210 of method 200. Instructions executed at processing unit 616 may enable processing unit 616 to receive a clock signal, such as from clock 620, and associate timing values with signals received from one or more sensors of sensor array 606.

Figure 7A:
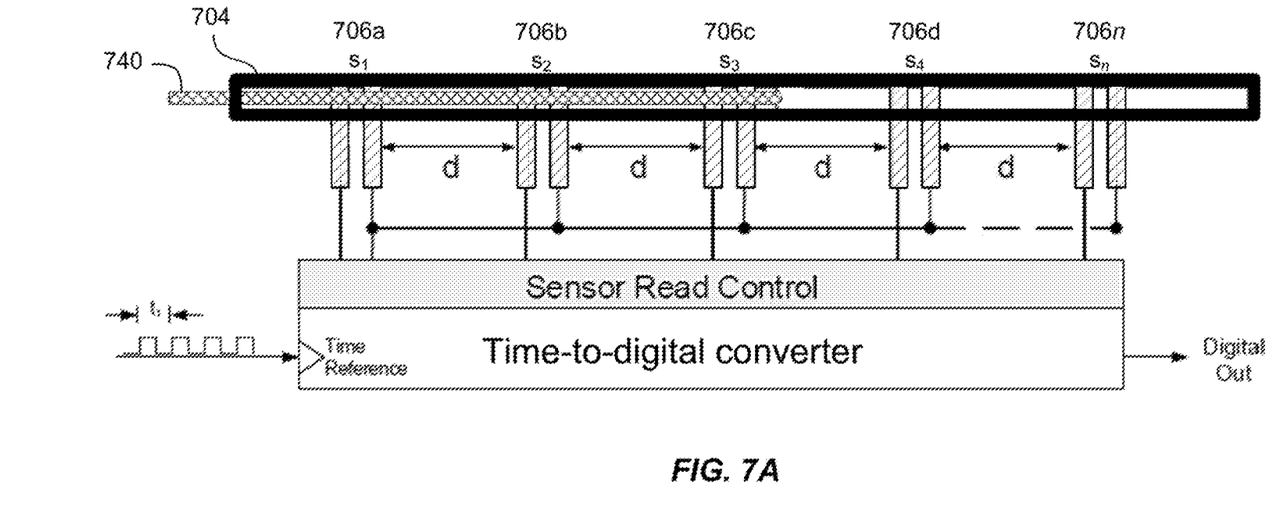
FIG. 7A illustrates an example linear sensor arrangement of a device for determining fluid properties.

FIG. 7A illustrates possible operation of a processing unit, such as processing unit 616, and possible function upon execution of instructions 614 according to one example. For example, FIG. 7A includes a capillary channel 704 receiving a fluid 740. An array of sensors, 706a-706n refer to a plurality of electrode pairs, $s_1$-$s_n$, arranged along capillary channel 704 equidistantly so as to be separated by a distance d. Signals from sensors 706a-706n are transmitted to a sensor read control component (e.g., a portion of a processing unit executing instructions to enable it to receive and interpret signals from sensors of a sensor array into fluid position indications). A clock signal, such as from clock 620 of FIG. 6, may be received at a time-to-digital converter component (e.g., a portion of a processing unit executing instructions to enable it to receive a clock signal and associate signals received from the sensor read control component, such as signals indicative of a fluid position, with timing values).

In one implementation, a counter, such as counter 618 in FIG. 6, may be incremented with each clock cycle. The counter value at a moment at which a sensor detects the presence of a fluid may be stored, such as in a memory (e.g., memory 612). Referring to FIG. 7A, the received clock signal cycles every $t_1$ units of time. Thus, for example, if the clock cycle six times in a period of time for fluid 740 to travel from sensor 706a to 706b, then a counter (e.g., counter 618) will have a value of 6 at the time at which fluid 740 is detected by the electrode pair of sensor 706b. That value may be stored in a portion of a memory, such as memory 612, and/or used to associate a timing value with a position value. In this example case, the timing value of six clock cycles may be used in conjunction with a position corresponding to sensor 706b by time-to-digital converter to yield an output usable for determining a flow rate, such as consistent with the discussion of block 210 of method 200.

Figure 7B:
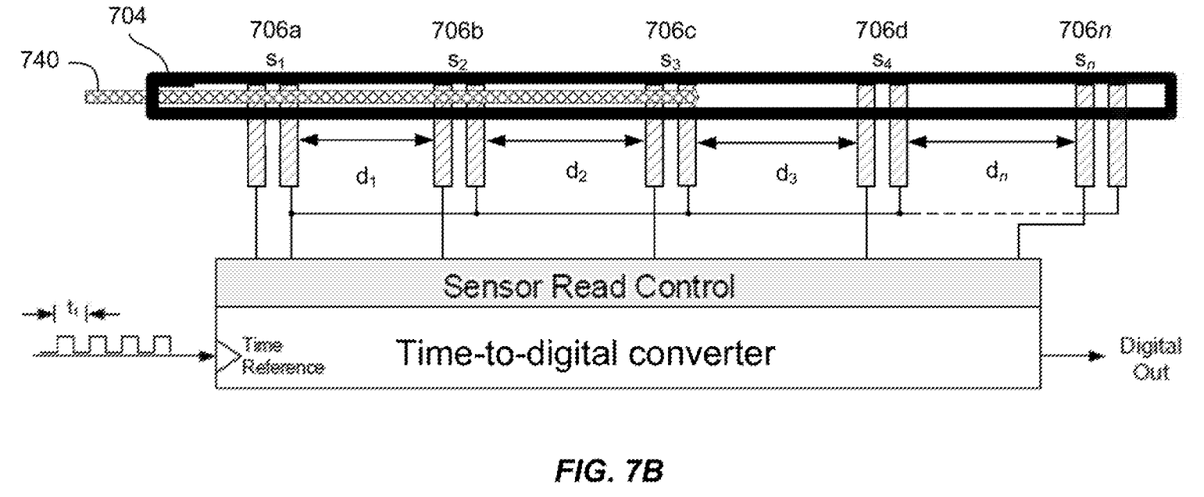
FIG. 7B illustrates an example non-linear sensor arrangement of a device for determining fluid properties.

In the example of FIG. 7A, if it is assumed that fluid 740 travels through capillary channel 704 at a constant flow rate (which may not be the case in at least some situations, as discussed above), then when flow rates are calculated based on clock signals and signals from sensors 706a-706n, the determined flow rates should be substantially the same. In contrast, FIG. 7B illustrates an example in which sensors 706a-706n of a sensor array are arranged non-linearly, as illustrated by varying distances, $d_1$-$d_n$, separating the electrode pairs. In the case of non-linearly arranged sensors, a fluid 740 traversing capillary channel 704 at a constant flow rate will not result in a series of the same counter values. For example, there may be six clock cycles in the time it takes fluid 740 to travel from sensor 706a to 706b, seven clock cycles in the time it takes fluid 740 to travel from sensor 706b to 706c, eight clock cycles in the time it takes fluid 740 to travel from sensor 706c to 706d, and 6+n clock cycles in the time it takes fluid 740 to travel from sensor 706d to 706n, by way of non-limiting example.

However, as noted above, in implementations in which fluid 740 is impelled by capillary forces, a flow rate of fluid 740 may decrease as fluid 740 advances into capillary channel 704. Thus, sensor read control component and time-to-digital converter component may be able to take the variable distance into account while associating fluid position and timing values.

Figure 8:
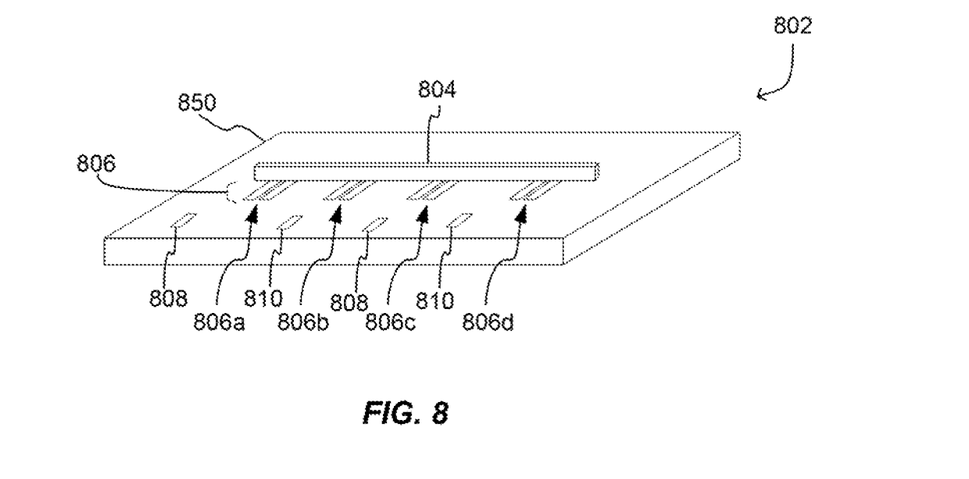
FIG. 8 is a perspective view of an example device for determining fluid properties.

FIG. 8 is an illustration of a device 802, similar to device 602 in FIG. 6, capable of determining parameters of a fluid. It is to be understood that the illustration of device 802 may comprise but a portion of a larger device comprising other components, such as, for example, a processor, memory, clock, bus, etc. By way of further example, for clarity, FIG. 8 does not illustrate communication lines or connectors (e.g., pins) between electrodes of sensor array 806 device, nor does FIG. 8 illustrate a fluid entry or exit to capillary channel 804, etc. FIG. 8 is thus presented by way of illustration of a simplified example arrangement of components of device 802 according to one implementation. In one example, device 802 may comprise a plurality of components, such as capillary channel 804, sensor array 806, temperature sensors 808, thermal elements 810, by way of non-limiting example, arranged on a substrate 850. The components of device 802 may comprise discrete components or may comprise components integrated into device 802, such as part of a fabrication process (e.g., a CMOS fabrication process), by way of example.

Figures 9A, 9B:
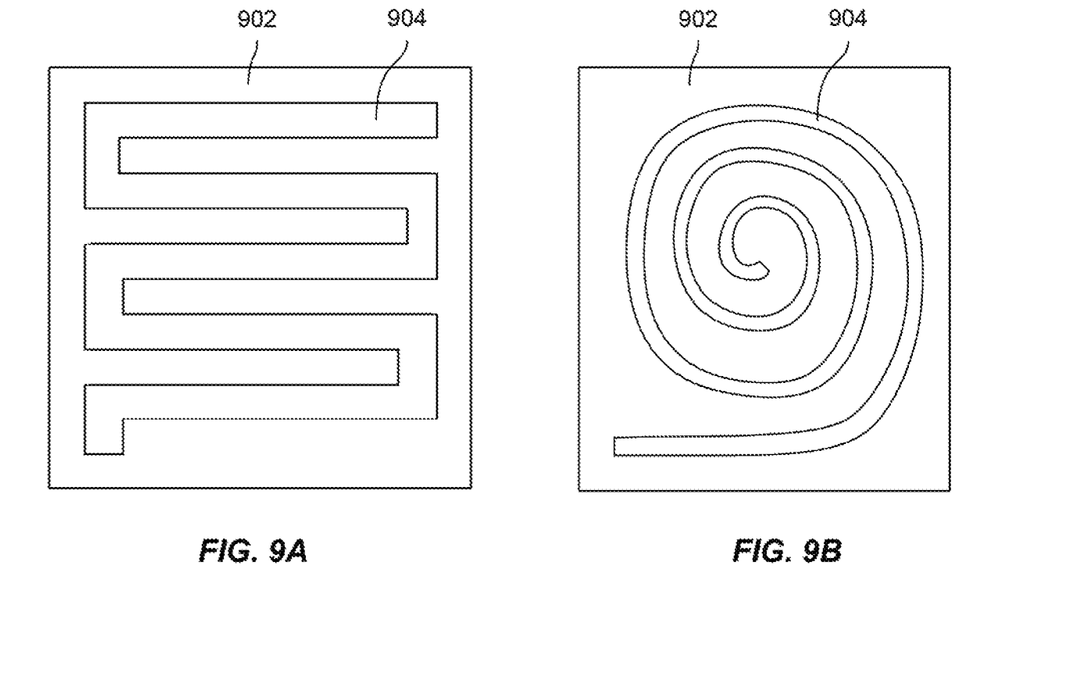
FIG. 9A is a top-down view of an example device with a serpentine capillary channel arrangement.
FIG. 9B is a top-down view of an example device with a spiral capillary channel arrangement.

FIG. 8 illustrates capillary channel 804 as rectangular in form, but as discussed above, capillary channel 804 may alternatively have a cylindrical form. Also, while capillary channel 804 is straight in FIG. 8, it may also be serpentine or spiral in form. FIG. 9A comprises a device 902 according to one implementation having a serpentine form of capillary channel 904. FIG. 9B comprises a device 902 according to another implementation having a spiral form of capillary channel 904. Returning to FIG. 8, it is noted that capillary channel 804 may be in fluid communication with a reservoir, such as reservoir 622 of FIG. 6 and/or an output receptacle (not shown). In one example, capillary channel 804 may be formed by installing a capillary tube on or in proximity to device 802. In an alternative example, capillary channel 804 may be formed with successive layers of polymer (e.g., spin coat) on substrate 850.

In an implementation in which sensor array 806 comprises electrochemical sensors, pairs of electrodes may be arranged in proximity to capillary channel 804. As discussed above, individual sensor pairs of sensor array 806 may be arranged along capillary channel 804 so as to determine a presence of fluid. For example, if a fluid is detected at sensor 806a but not at sensor 806b-806d, then fluid position may be determined to be limited to a portion of capillary channel 804 corresponding to 806a. By contrast, if sensors 806a-806c detect a fluid, then it may be determined that a position of fluid corresponds to a portion of capillary channel 804 corresponding to sensors 806a-806c. Furthermore, if sensor array 806 comprises electrochemical sensors, it may be possible to measure a conductivity value of a fluid in capillary channel 804. For example, if a fluid is present in capillary channel 804, a conductivity at a sensor electrode pair may be higher or lower (e.g., such as based on an ionic concentration of the fluid) than an expected conductivity value for the fluid. In one implementation, multiple conductivity measurements of a fluid may be aggregated and averaged to yield a conductivity measurement of the fluid.

In an implementation comprising capacitive sensors of sensor array 806, insulated conducting electrodes may be arranged in capillary channel 804 and fluid in contact with the electrodes of sensor array 806 may form a capacitive layer at an interface between the fluid and the electrode(s). A simple potential step or alternating potential signal may be applied to the electrodes and charge transfer at a dielectric region of the fluid-electrode capacitive layer may be measured, such as at processing unit 616. Fluid in capillary channel 804 may have its own dielectric region that may be different from the dielectric region at the fluid-electrode interface. The dielectric region at the fluid-electrode interface and the fluid dielectric region may have a combined dielectric (or permittivity) value different from (e.g., greater than) the permittivity of the air present between a pair of dry electrodes. As such, dynamic voltage techniques may be used to measure the charge transfer response at the electrodes to detect the presence or lack of fluid at the interface. For example, because in one case, charge transferred in or out of a capacitive structure is proportional to a change in potential across the capacitor and the capacitance value: $I_C = C^* \Delta V/\Delta T$, where $I_c$ is the current through the capacitor and $\Delta V/\Delta T$ is the change in voltage across the capacitor over a given time. Thus any change in C for a given $\Delta V/\Delta T$ will produce current $I_c$ that can be easily measured and compared to a calibration value. Further, a constant $I_c$ can be applied for a precise time $\Delta T$ and a resulting $\Delta V$ measured characteristic of the capacitance value.

It is noted that in some cases, the use of capacitive sensors in sensor array 806 may enable estimation of conductivity of a fluid. For example, for some fluids, the dielectric properties of the fluid may be related to ionic salt concentration thereof (e.g., and the conductivity of the fluid). Thus, a capacitive sensing method may be capable of measuring a conductivity of solution fluid. An aggregate set of capacitive measurements may provide an averaged measure of dielectric properties of a fluid, for example.

In a further implementation, fluids may be detected within capillary channel 804 using optical sensors for sensor array 806. In one case, optical sensing may comprise use of photo sensitive detectors along capillary channel 804 which may receive electromagnetic radiation (e.g., visible light) from one or more sources to allow a position of a fluid within capillary channel 804 to be determined, such as based, at least in part, on changes to electromagnetic radiation detected at photo-sensitive detectors of sensor array 806. For example, as a fluid passes over a photo sensitive detector, light traversing the fluid may scatter and less light may reach the photo detector thus indicating the presence of the fluid. In one implementation, a signal received from the photo sensitive detectors may comprise a binary indication of fluid presence.

As discussed above, a capillary channel may be used in order to determine properties of fluids. For instance, an array of sensors may be arranged in proximity to a capillary channel to determine presence of a fluid within the capillary channel. The fluid presence determinations may be used to determine a flow rate of the fluid, which may enable determination of a fluid viscosity. At times, it may be desirable to determine a measure of coagulation of the fluid using the viscosity determination. Furthermore, a thermal sensor and thermal element may be used to control temperature an environment surrounding the capillary channel.

In the preceding description, various aspects of claimed subject matter have been described. For purposes of explanation, specifics, such as amounts, systems and/or configurations, as examples, were set forth. In other instances, well-known features were omitted and/or simplified so as not to obscure claimed subject matter. While certain features have been illustrated and/or described herein, many modifications, substitutions, changes and/or equivalents will now occur to those skilled in the art. It is, therefore, to be understood that the appended claims are intended to cover all modifications and/or changes as fall within claimed subject matter.

What is claimed is:

1. An article comprising:
 a non-transitory computer-readable medium having instructions stored thereon executable by a processor to:
  determine a presence of a fluid in a capillary channel based on a signal received from a sensor of an array of sensors arranged along the capillary channel;
  determine a flow rate of the fluid traversing the capillary channel based on the received signal;
  determine a viscosity of the fluid based on the flow rate;
  determine a temperature of an environment surrounding the capillary channel based on a signal received from a thermal sensor arranged in proximity to the capillary channel; and
  transmit a signal to a thermal element arranged in proximity to the capillary channel responsive to the signal received from the thermal sensor to provide temperature control based on the temperature of the environment.

2. The article of claim 1, wherein the array of sensors are arranged non-linearly along the capillary channel and wherein the instructions further comprise instructions executable by the processor to:
 increment a counter responsive to cycles of a clock signal; and
 store a counter value responsive to detection of the presence of the fluid at the sensor of the array of sensors.

3. The article of claim 1, wherein the instructions further comprise instructions executable by the processor to:
 determine a rate of change of the flow rate of the fluid; and
 determine a rate of change of the viscosity based on the rate of change of the flow rate, wherein the processor is to determine the temperature of the environment surrounding the capillary channel in parallel with the transmission of the signal to the thermal element.

4. The article of claim 3, wherein the instructions further comprise instructions executable by the processor to:
 determine a measure of coagulation of the fluid based on the determined rate of change of the viscosity of the fluid.

5. An apparatus comprising:
 a capillary channel coupled to a fluid reservoir, wherein the capillary channel and the fluid reservoir are arranged to transmit fluids through the capillary channel responsive to capillary forces;
 an array of sensors arranged along the capillary channel, the sensors arranged non-linearly along the capillary channel, wherein the array of sensors is to determine a presence of a fluid in the capillary channel, a determination of a flow rate of the fluid based on the determined fluid presence, and a determination of a viscosity of the fluid based on the determined flow rate;
 a plurality of thermal sensors arranged in proximity to the capillary channel, wherein the plurality of thermal sensors are to measure a temperature of an environment surrounding the capillary channel; and
 a plurality of thermal elements arranged in proximity to the capillary channel, wherein the plurality of thermal elements are to provide temperature control based on the temperature of the environment.

6. The apparatus of claim 5, wherein the array of sensors is further to:
 determine a rate of change of the flow rate; and
 determine a rate of change of the viscosity based on the rate of change of the flow rate.

7. The apparatus of claim 6, wherein the array of sensors is further to:
 determine a measure of coagulation based on the determined rate of change of the viscosity of the fluid.

8. The apparatus of claim 5, wherein the non-linear spacing of the sensors of the array of sensors is such that a first distance between a first pair of sensors of the array of sensors is different from a second distance between a second pair of sensors.

9. The apparatus of claim 5, wherein the sensors of the array of sensors comprise electrochemical sensors.

10. The apparatus of claim 5, wherein the sensors of the array of sensors comprise capacitive sensors.

11. The apparatus of claim 5, wherein the capillary channel has a serpentine or spiral form.

12. The apparatus of claim 5, further comprising a clock and a processor that receives a clock signal from the clock, and the processor is further to:
 increment a counter responsive to cycles of the clock signal; and
 store a counter value responsive to detection of the fluid at a sensor of the array of sensors.

13. The apparatus of claim 5, wherein the capillary channel, the array of sensors, the plurality of thermal elements, and the plurality of thermal sensors are arranged in a complementary metal-oxide-semiconductor (CMOS) device.

14. The apparatus of claim 13, wherein the CMOS device comprises a lab-on-a-chip device.

15. A method comprising:
 determining, using a processor of an apparatus, a presence of a fluid in a capillary channel of the apparatus, the apparatus being arranged to transmit the fluid via the capillary channel using capillary forces, wherein determining the presence of the fluid is based at least in part on signals received from a sensor of an array of sensors of the apparatus, the array of sensors being arranged along the capillary channel, and further wherein the apparatus comprises a fluid property measurement apparatus;
 determining, using the processor, a flow rate of the fluid based on the received signals;
 determining, using the processor, a viscosity of the fluid based on the flow rate;
 determining a measure of coagulation based on the determined flow rate;
 determining a temperature of an environment surrounding the capillary channel using a plurality of thermal sensors arranged in proximity to the capillary channel; and transmitting a signal to an element of a plurality of thermal elements, arranged in proximity to the capillary channel, based on the determined environmental temperature.

16. The method of claim 15, wherein the array of sensors are arranged non-linearly along the capillary channel, the method further comprising determining a rate of change of the viscosity of the fluid based on a plurality of viscosity determinations.

17. The method of claim 16, wherein determining the measure of coagulation is based on the determined rate of change of the viscosity of the fluid.

18. The method of claim 17, wherein the fluid comprises blood, and the method further comprising providing temperature control to the environment in response to transmitting the signal to the element of the plurality of thermal elements.

19. The method of claim 15, further comprising varying a temperature of the environment by transmitting a plurality of signals to the element of the plurality of thermal elements, the plurality of signals including the signal, and wherein the capillary channel, the array of sensors, the plurality of thermal elements, and the plurality of thermal sensors are arranged on a substrate.

20. The method of claim 15, wherein determining the rate of change of the flow rate of the fluid comprises:
receiving, at the processor, a clock signal from a clock;
incrementing a counter based on cycles of the clock signal; and
storing a counter value responsive to detection of the fluid at a sensor of the array of sensors.

* * * * *